United States Patent
Backlund et al.

(12) 
(10) Patent No.: US 6,280,983 B1
(45) Date of Patent: Aug. 28, 2001

(54) ENZYME IMMOBILIZATION IN A GEL CONTAINING 30 TO 50 PERCENT GELATIN

(76) Inventors: Sune Backlund, Tennbyvägen 30 lok. 26, FIN-21600 Pargas; Folke Eriksson, Kilavägen 1, FIN-10300 Karis; Gun Hedström, Patisvagen 1103, FIN-21330 Patis; Stefan Karlsson, Tegelslagaregatan 15 a D 33, FIN-20810 Åbo, all of (FI)

( * ) Notice: Subject to any disclaimer, the term of this patent is extended or adjusted under 35 U.S.C. 154(b) by 0 days.

(21) Appl. No.: 09/242,268

(22) PCT Filed: Aug. 25, 1997

(86) PCT No.: PCT/FI97/00489

§ 371 Date: Feb. 12, 1999

§ 102(e) Date: Feb. 12, 1999

(87) PCT Pub. No.: WO98/08942

PCT Pub. Date: Mar. 5, 1998

(30) Foreign Application Priority Data

Aug. 27, 1996 (FI) ........................................ 963323

(51) Int. Cl.⁷ .................. C12P 7/64; C12P 7/62; C12P 41/00; C12N 11/02; C12N 11/10
(52) U.S. Cl. .................. 435/134; 435/135; 435/177; 435/178; 435/182; 435/280
(58) Field of Search ................... 435/134, 135, 435/174, 177, 178, 180, 182, 280

(56) References Cited

U.S. PATENT DOCUMENTS

| | | | | |
|---|---|---|---|---|
| 4,254,227 | * | 3/1981 | Okada et al. | 435/97 |
| 4,411,999 | | 10/1983 | Shigesada et al. | 435/177 |
| 4,912,032 | * | 3/1990 | Hoffman et al. | 435/7 |
| 4,978,619 | * | 12/1990 | Kajiwara et al. | 435/182 |
| 5,292,649 | * | 3/1994 | Kosugi et al. | 435/134 |
| 5,378,627 | * | 1/1995 | Shibatani et al. | 435/280 |
| 5,776,741 | * | 7/1998 | Pedersen et al. | 435/134 |

FOREIGN PATENT DOCUMENTS

| | | |
|---|---|---|
| 0 056 111 A1 | 7/1982 | (EP) . |
| 0 068 594 A1 | 1/1983 | (EP) . |
| 1 500 456 | 2/1978 | (GB) . |

OTHER PUBLICATIONS

Koch et. al., "Enzymatic Catalysis in Organic Media: Reactors with a Solidified Water–Phase", Biochem. Eng. vol. 3, pp. 58–60 (3rd Int. Symp. 1995).*

"Immobilized Biocatalysts", Ullmann's Encyclopedia of Industrial Chemistry. (5th ed), vol. A14, pp. 40–41 (1989).*

Tosa et al., "Immobilization of Enzymes and Microbial Cells . . . " Biotech. and Bioeng., vol. XXI 1697–1709 (1979).

Koch et al., "Enzymatic Catalysis in Organic Media: . . . " Aachen University of Technology, Dept. of Biotechnology, D–52076 Aachen (Germany).

Ullmann's Encyclopedia of Industrial Chemistry, (5th ed) vol. A14, pp. 40–41.

* cited by examiner

Primary Examiner—David M. Naff
(74) Attorney, Agent, or Firm—James C. Lydon

(57) ABSTRACT

Gel immobilized enzymes are prepared for use in carrying out reactions in hydrophobic solvents. The gel is formed from a gelatinizer such as gelatin or a polysaccharide such as agarose, agar, pectin, sodium alginate or carrageenan. The gel contains a ratio of amount of gelatinizer to amount of water such that the gel is capable of being mechanically divisible into dimensionally substantially stable fragments at a temperature which may reach a lower limit of the gelation temperature range of the gelatinizer. A preferred gel contains 30 to 50% gelatin, and is prepared by forming a mixture of water, enzyme and water-soluble gelatin, heating the mixture to dissolve the gelatin to form a solution, and cooling the solution until it forms a gel. An immobilized lipase can be used for synthesis of an optically active isomer of an ester from an alcohol and an acid, with either the alcohol or the acid being a racemic mixture or an enantiomer, for hydrolysis of an ester which is either a racemate or a pure enantiomer, or for transesterfication.

11 Claims, 4 Drawing Sheets ly have to be perfectly pure and above all, free from toxic
ENZYME IMMOBILIZATION IN A GEL CONTAINING 30 TO 50 PERCENT GELATIN This application is a U.S. national stage of International Application PCT/FI97/00489, filed Aug. 25, 1997, and published on Mar. 5, 1998 in the English language.

BACKGROUND OF THE INVENTION

1. Field of the Invention

The present invention relates to a gel containing an immobilised enzyme, a method for preparing such a gel and its application in enzyme-catalysed reactions in hydrophobic solvents.

2. Description of the Related Art

Enzyme-catalysed reactions are in widespread use particularly in foodstuffs and pharmacological chemistry. Some enzymes being very expensive, it is essential that they are carefully recovered for re-use in subsequent reactions. This can be done by immobilising the enzymes on solid supports e.g. in the form of small solid beads which are introduced in the reaction mixture and separated after the reaction has been accomplished. Continuous reactions may be performed by placing these beads in a column and by allowing the reaction mixture to flow through the bed of beads. In such beads, the enzyme is covalently bound into a compound, e.g. a polymer containing reactive groups reacting with the amino groups in the protein part of the enzyme.

The work Koskinen A. M. P. & Klibanov, A. M. Blackie Academic & Professional, Glasgow 1996 describes methods for immobilising an enzyme on a solid support in the section "Modes of using enzymes in organic media" by P. Adlercreutz. The methods may be summarised as follows:

- an aqueous solution containing the enzyme is brought into contact with a solid support, water is removed under reduced pressure and the enzyme is precipitated onto the solid support;
- the enzyme is precipitated from an aqueous solution in the presence of a solid support, the precipitation taking place with the addition of a cooled, water-miscible solvent, such as acetone;
- the enzyme in the aqueous solution is allowed to spontaneously adsorb on a solid support;
- the enzyme is covalently bound to a solid support, and
- the enzyme, which is adsorbed or precipitated on a solid support, is cross-linked with glutaraldehyde.

The publication S. Backlund et al., *Kamia-Kemi* Vol. 20 (1993) 197–201 describes an enzyme-catalysed synthesis of a number of esters by means of the enzyme lipase incorporated in a water-in-oil microemulsion. The publication S. Backlund et al., Colloid Polym Sci 274:540–547 (1996) describes a lipase-catalysed synthesis of optically active esters from racemic 2-octanol and various carboxylic acids. The lipase is incorporated in a microemulsion-based gel, in which the microemulsion is either a water-in-oil microemulsion or a microemulsion having a bicontinuous structure.

However, the above methods for immobilising enzymes involve a large number of drawbacks. Above all, the immobilising methods described above are very sophisticated, laborious and expensive.

Precious enzymes are used e.g. in the preparation of optically active pharmaceutical compounds, which obviously have to be perfectly pure and above all, free from toxic substances. In this conjunction, polymers and similar enzyme-binding substances may involve an undesired risk. Hydrocarbons are for instance used as a hydrophobic component in the preparation of microemulsions. Surfactants are used to stabilise microemulsions, AOT (sodium 1,4-bis(2-ethylhexyl)sulfosuccinate) being probably the most common of these. The AOT surfactant is not suitable for use in pharmaceutical contexts.

EP patent application 68594 describes a gel consisting of water, enzyme, gelatiniser, buffer, and albumine or protein. The albumine or protein component is allegedly added to stabilise the enzymic system. The gel thus produced will have the form of small beads. Judging by the disclosure, the mixture used is unlikely to have resulted in a gel which is mechanically divisible into fragments at a temperature equalling at least approximately the gelatination temperature of the gelatiniser or at the ambient temperature. The disclosure indicates that the mixture was cooled down to 5° C. Cooling to such a low temperature implies that bead formation would have been impossible at a higher temperature.

The publication Biotech. Bioeng. 21 (1979) 1697–1709 (Tosa et al) describes a gel with carrageenan as a gelatiniser. The gel was shaped as a cube at a low temperature (10° C.). There is no suggestion of the possibility to divide this gel mechanically at the gelatination temperature of carrageenan or in the proximity of this.

SUMMARY OF THE INVENTION

The purpose of the present invention is to achieve a straightforward gel providing ease of production and handling and containing an enzyme immobilised within it. A further purpose is that such a gel be free from toxic substances and thus suitable for pharmaceutical synthesis. Moreover, none of the components in the gel should act as a substrate for the enzyme. Still a further purpose is to provide a gel having a surface with open pores such that the enzyme immobilised within the gel is well contacted with the surrounding reaction mixture. The purpose is also to enable the reaction to be performed at the ambient temperature without stirring, which is an economical procedure in terms of energy supply.

Thus, the invention relates to a gel containing an immobilised enzyme. The gel is characterised in that it consists of a water-soluble enzyme, a water-soluble gelatiniser and water, the ratio of the amount of gelatiniser to the amount of water having been selected such that the gel formed can be mechanically divided into dimensionally substantially stable fragments at a temperature which can reach the lower limit of the gelatination temperature range of the gelatiniser.

DETAILED DESCRIPTION OF THE PREFERRED EMBODIMENTS

Figure 1:
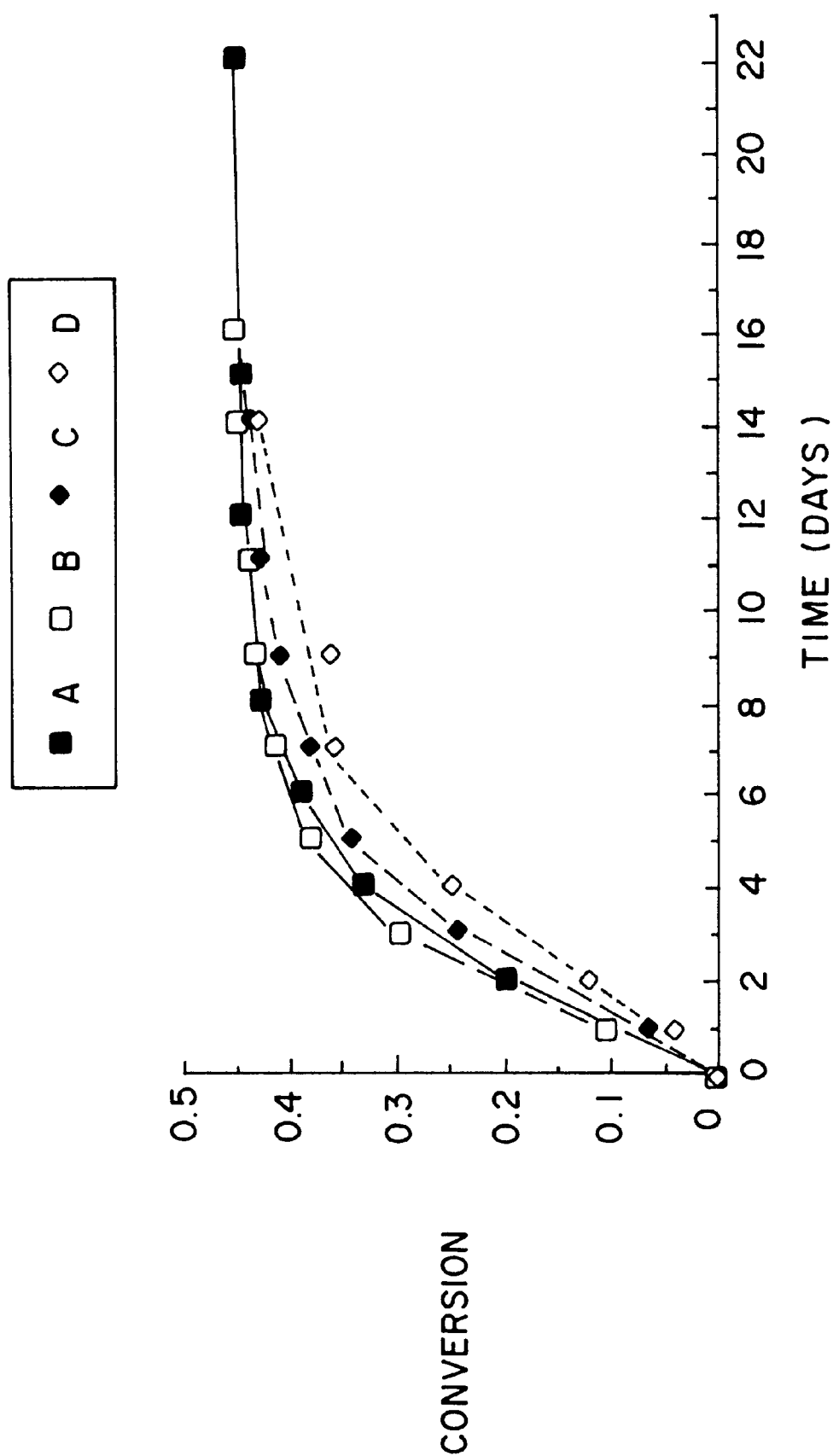
FIG. 1 shows the synthesis of optically active isomers of 2-octylhexanoate from racemic 2-octanol and hexanoic acid as a function of time, with the use of four mutually identically gels (A–D) containing gelatin, lipase and water.

In the following, the term "immobilising" implies that the enzyme is immobilised by being dissolved in a hydrogel, i.e. a gel with water as the solvent.

The wording "mechanically divisible into dimensionally substantially stable fragments" signifies that one should be able to cut the gel into fragments which can be handled and conserved without losing their ease of handling during storage. Likewise, it is crucial that this gel will remain intact in the hydrophic solvent in which the gel is to be used.

Substances suitable as gelatinisers are for instance gelatin or polysaccharides such as agarose, agar, pectin, sodium alginate or carrageenan.

With gelatin as a gelatiniser, the gel will have a 20 to 50% gel concentration, preferably 30 to 44%. The corresponding ranges for agar and sodium alginate are 5 to 20% and 10 to 15%, respectively.

The gel of this invention is prepared by adding to the water-soluble gelatiniser an amount of water selected such that the gel formed will be mechanically divisible into dimensionally substantially stable fragments at a temperature that may reach the lower limit of the gelatination temperature range of the gelatiniser. The mixture obtained is heated to a temperature at which the gelatiniser dissolves in water (approx. 50° C. for gelatin and approx. 90° C. for agar), upon which the solution thus obtained is cooled until it is gelatinised.

Most gelatinisers have a gelatination temperature in the range of 30 to 40° C. Sodium alginate is gelatinised by adding $Ca^{2+}$ ions and this is the reason why they are appropriately prepared at the ambient temperature e.g. in a 0.05 M $CaCl_2$ solution.

Even though the gels of the invention can be cut into dimensionally stable fragments at temperatures which may reach the lower limit of the gelatination temperature range of the gelatiniser, in practical implementation, the gel is appropriately cut at the ambient temperature or at a somewhat lower temperature (approx. 18 to 25° C.).

The gel is used in enzyme-catalysed reactions in which the reactants are dissolved in a hydrophobic solvent. Gel fragments containing the gel are contacted with the reactants, the reaction occurring at the interface between the gel and the hydrophobic solvent. Porous gel fragments will be particularly suitable, since the reaction solution penetrates into the pores of the gel fragments. This increases the interface at which the enzyme-catalysed reaction takes place.

With lipase as the immobilised enzyme, the gel will be suitable for synthesis of optically active esters from racemic alcohols and carboxylic acids, or for the preparation of optically active alcohols or carboxylic acids by hydrolysis of racemic esters, or for reesterifications.

The invention will be described in greater detail below by means of an embodiment example. All of the experiments comprised synthesis of optically active isomers of 2-octylhexanoate from racemic 2-octanol and hexanoic acid. The test results are illustrated with figures

EXAMPLE

Materials

The following reactants were used in the experiments: gelatin type B, 710 $\mu$m, approx. Bloom 230 supplied by the University Pharmacy of Turku, (±)-2-octanol (approx. 98%) and hexanoic acid (>98%) from Fluka, hexane (p.a.) from Merck, 4-dimethylaminopyridine (DMAP), acetic acid anhydride (>98%) and pyridine (HPLC degree) from Sigma Chemicals, and lipase Candida sp. (SP525) from Novo Nordisk, Denmark. (±)-2-oxtylhexanoate (approx. 95%) was chemically synthesised. The water was distilled deionised.

Methods a) Preparation of gel

The gelatin and the water into which the lipase had just been dissolved were heated to 50° C. while stirring for about 5 to 7 minutes to make the gelatin dissolve. The solution was stabilised at 30° C. for one hour, after which the pseudosolid aquatic gel (PAG) was conserved at −20° C. until it was used.

b) Reaction

The pseudosolid gel (PAG) was cut into about 25 fragments at the ambient temperature and was transferred into a 100 ml E retort. A hexane solution containing 0.33 M (±)-2-octanol and 0.33 M hexanoic acid for synthesis (or 0.33 M (±)-2-oxtyl hexanoate for hydrolysis) was introduced in the retort, the reaction being then initiated. The reactions were performed at 25° C. without shaking the reaction retort.

c) Sampling and analysis

At the end of given intervals samples (usually of 0.150 $cm^3$) were taken from the reaction solution in order to monitor the reaction process. The samples were acetylised with acetic acid anhydride. DMAP dissolved in pyridine acted as a catalyst. The acetylised samples were analysed by means of a Varian 3400 gas chromatograph, to which a chiral column (Cyclodex-B from J & W Scientific; 30 m×0.252 mm with a film thickness of 0.25 $\mu$m) was coupled.

Results

Conversion

The areas for the reactants or substrates (s) and the reaction products (p) were read from the chromatograms. The conversion (c) was calculated with the formula $$c=ee_s/(ee_c+ee_p)$$

where $ee_c=(S1-S2)/(S1+S2)$ and $ee_p=(P1-P2)/(P1+P2)$. S1 or P1 corresponds to the area of the dominating enantiomer, while S2 or P2 corresponds to the area of the second enantiomer.

Reproducibility

Comparison of the synthesis process of four separate pseudosolid gels (A, B, C, D) with identical composition: The gelatin amount was 1.4 g and the water amount 1.8 g. All of the reactions reach a 0.45 conversion at the end of about 12 days, when equilibrium is achieved. A and B produce almost identical processes, whereas C and D have a somewhat lower initial rate. The results are presented in Table 1 and FIG. 1.

TABLE 1

Reproducibility. Gels A–D contained 43.8% of gelatin and 8.8 mg of lipase.

| Pseudosolid gel | Time (h) when c = 0.2 |
| --- | --- |
| A | 48 |
| B | 48 |
| C | 59 |
| D | 75 |

Re-use of the gels

Figure 2:
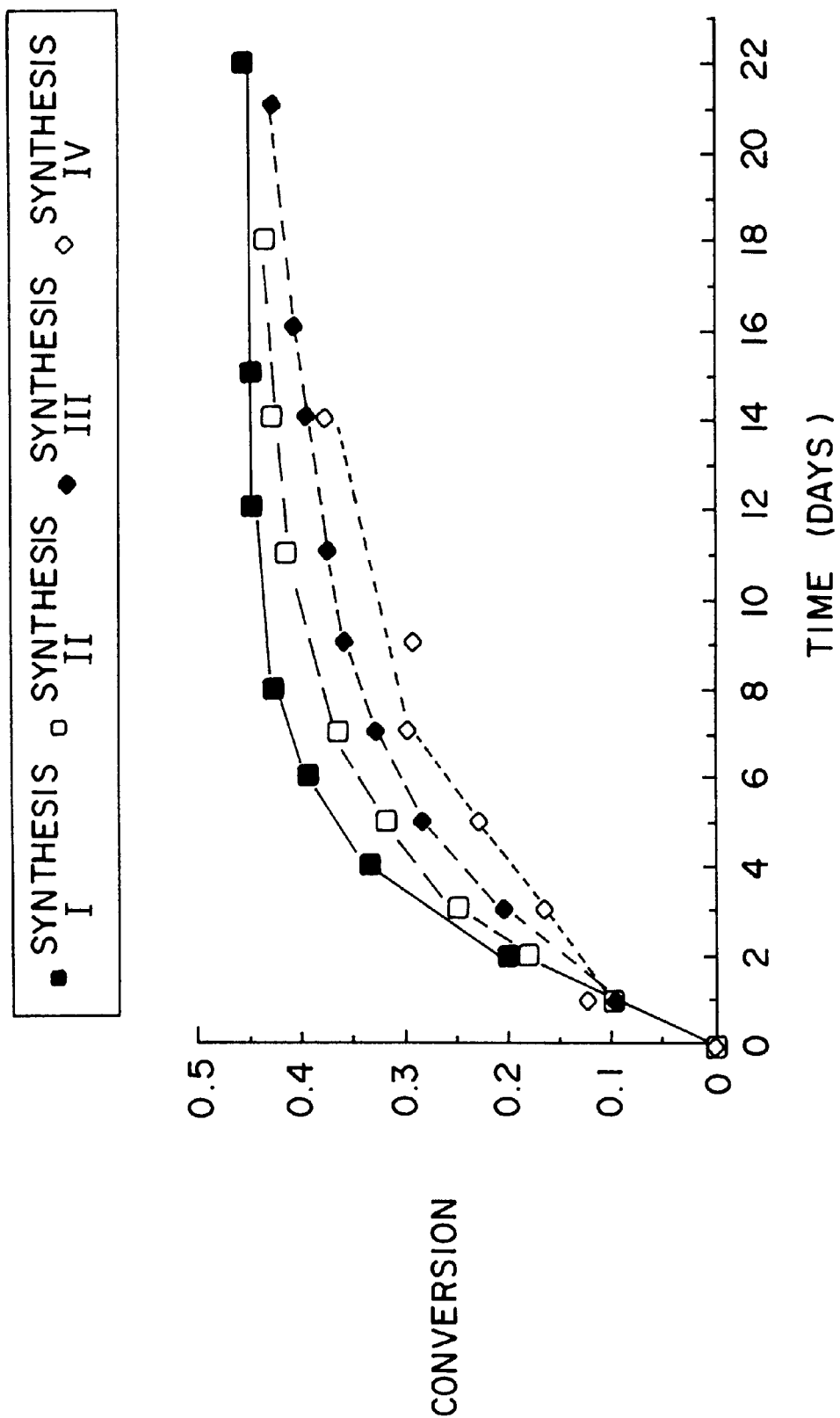
FIG. 2 shows the synthesis as a function of time with the use of a single gel in four successive syntheses I to IV.

The same pseudosolid gel was used four subsequent times in identical syntheses (I, II, III, IV). The gel was repeatedly rinsed with hexane between the cycles. The same conversion degree is probably obtained, however, the reaction will slow down for each re-use. The gel will also have caked to some extent. The results are shown in Table 2 and FIG. 2.

TABLE 2

Re-use. Gel composition: 43.8% of gelatin and 8.8 mg of lipase (1.4 g of gelatin and 1.8 g of water).

| Synthesis number | Time (h) when c = 0.2 |
|---|---|
| I | 48 |
| II | 54 |
| III | 72 |
| IV | 87 |

Enzyme amount

Figure 3:
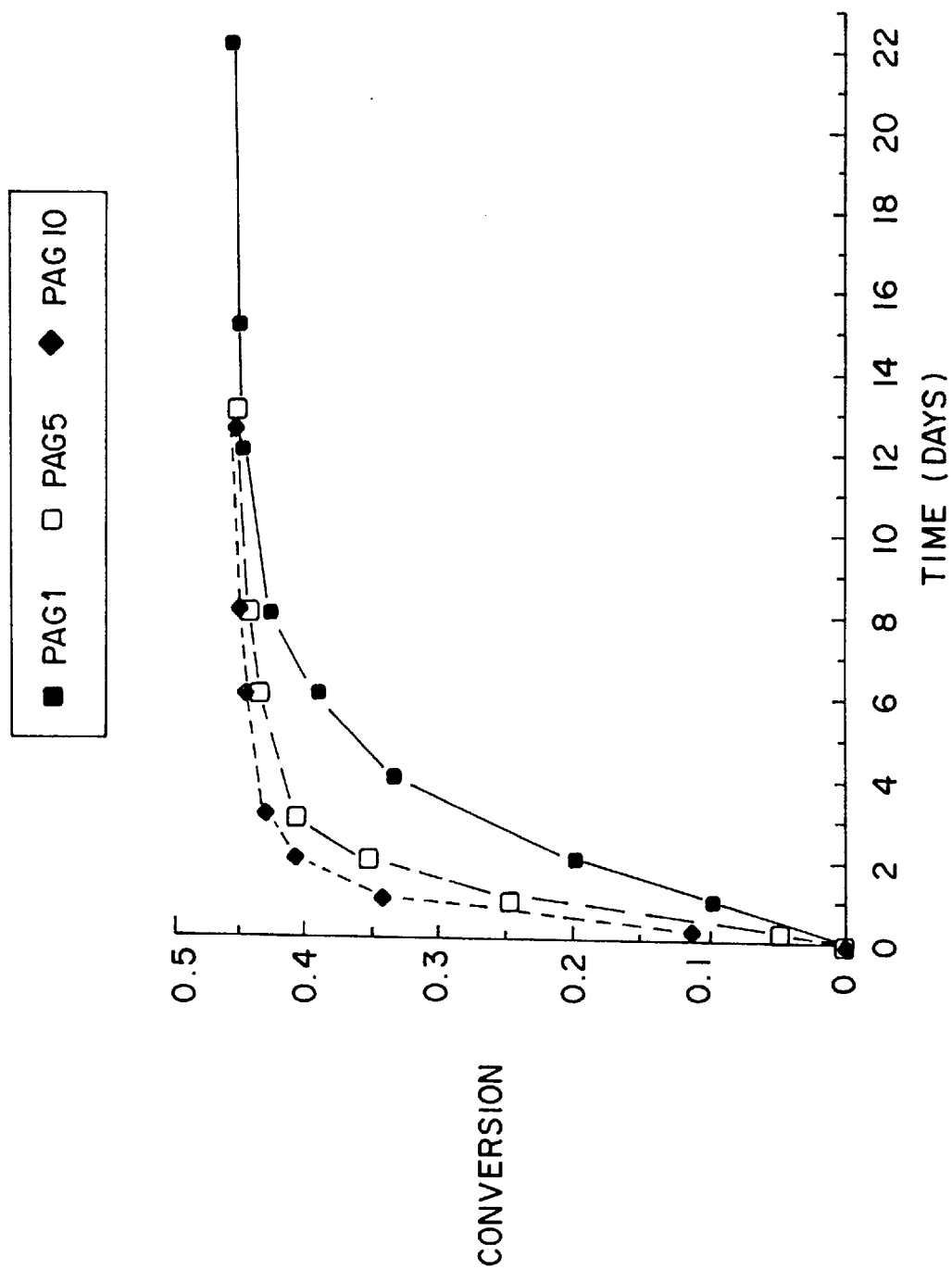
FIG. 3 shows the synthesis as a function of time with the use of three gels (PAG1, PAG5 and PAG10) containing different amounts of enzyme.

Pseudosolid gels with identical compositions (gelatin:water) but with different enzyme concentrations were mutually compared in a synthesis of the type described above. PAG1 contained 8.8 mg, PAG5 44 mg and PAG10 88 mg of lipase. The greater the amount of added enzyme, the faster the 0.45 conversion degree was achieved. The results are shown in Table 3 and FIG. 3.

TABLE 3

Impact of the enzyme amount. The gels contained 43.8% of gelatin (1.4 g of gelatin and 1.8 g of water).

| PAG | Enzyme amount mg | Time (h) when c = 0.2 | Max c | Time days | $ee_s$ | $ee_p$ |
|---|---|---|---|---|---|---|
| 1 | 8.8 | 48 | 0.45 | 12 | 0.80 | 0.99 |
| 5 | 44 | 19 | 0.45 | 8 | 0.80 | 0.99 |
| 10 | 88 | 12 | 0.45 | 6 | 0.80 | 0.99 |

Gelatin amount

Figure 4:
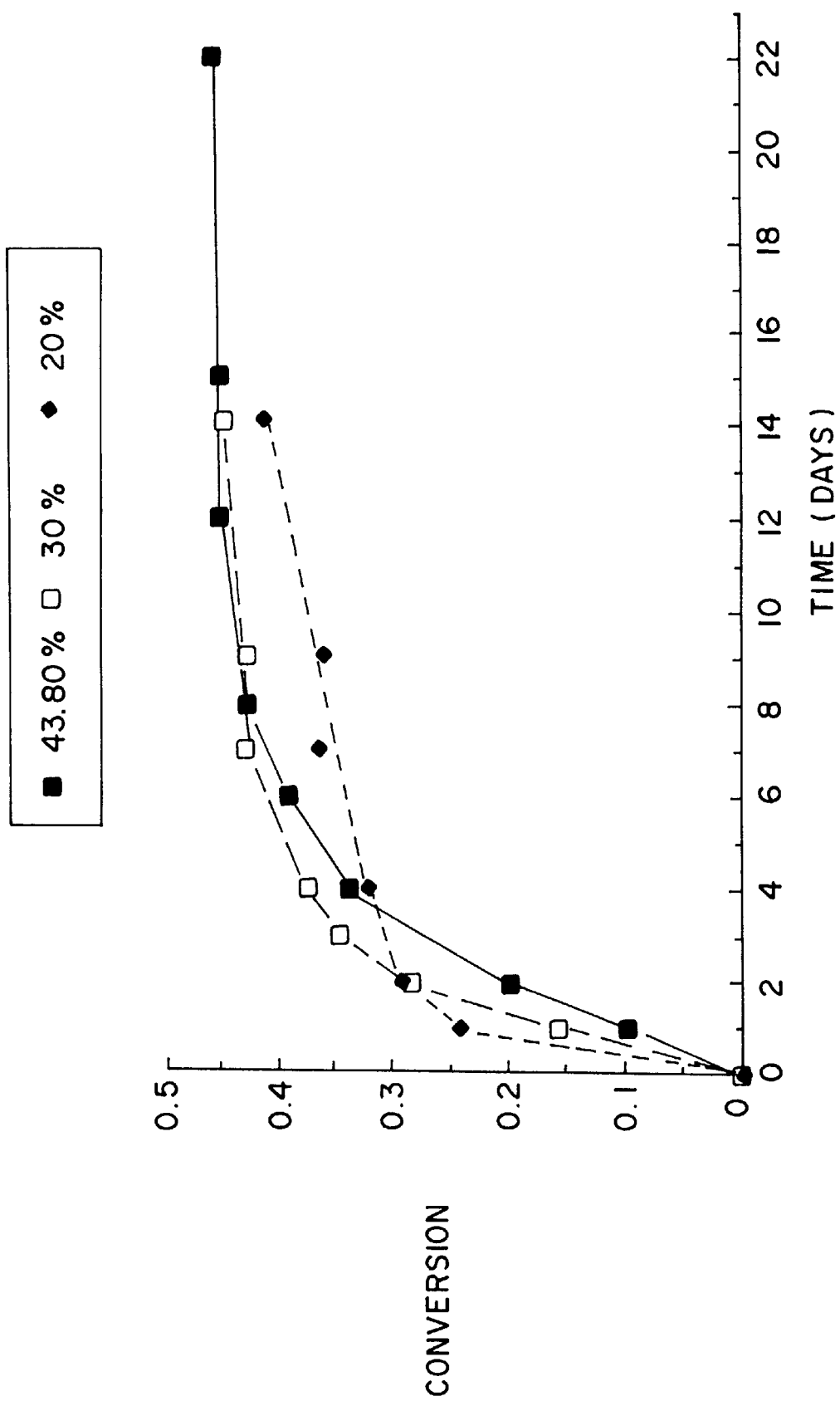
FIG. 4 shows the synthesis as a function of time with the use of three gels having different gelatin concentrations.

Pseudosolid gels having different gelatin concentrations (43.8%, 30%, 20%) were tested in syntheses of the kind described above. The pseudosolid gel becomes softer, the lower the gelatin concentration is. In hexane without substrates, gels with a less than 20% gelatin concentration remain stable, whereas used with a substrate, the gel pieces will cake relatively fast even for 20 and 30% gelatin, forming a mass full of lumps. The reaction is faster in softer pseudosolid gels, which, however, are also much faster destroyed. The results are shown in Table 4 and FIG. 4.

TABLE 4

Impact of the gelatin concentration. The gels contained 8.8 mg of lipase (gelatin 1.4 g).

| PAG | Gelatin % | Time when c = 0.2 | Max c | Time days | Observations |
|---|---|---|---|---|---|
| a | 43.8 | 48 | 0.45 | 12 | pieces |
| b | 30 | 32 | 0.45 | ≧15 | lumps |
| c | 20 | 21 | 0.45 | >15 | thick mass |

Reversibility

The hydrolysis conversion degree was examined by using the ester as a substrate. At the end of 14 days the conversion was in the range of 0.03 to 0.06 depending on the way it was calculated. In other words, this is a reversible process, with the reaction heavily displaced in the synthesis direction.

The experiments indicate that very high conversion and very high optical purity are achieved by using an enzyme immobilised in a gel in accordance with this invention. The gel may be re-used several times, with long intermediate storage. Compared with previous enzyme immobilising methods, this invention has the advantage of not requiring the use of any foreign substances, such as surfactants. This enables non-toxic and environment-friendly enzyme-catalysing processes to be implemented. At the same time, the risks of competing enzyme reactions are reduced. In addition, the process is energy-saving.

Compared with prior art, the gel in accordance with this invention has a number of appreciable advantages in being mechanically divisible into fragments, which dimensionally are at least almost stable during the actual division and subsequent use (for instance in stereoselective synthesis). The possibility of selecting the size and the shape of the gel fragment to be added to the reaction mixture provides a practical solution. After the reaction has been performed, recovery of the gel will be perfectly simple if the gel has the form of one single piece or a few pieces. A gel in the form of small (approx. 1 mm) beads requires a specific filtrating step, necessarily involving a given particle loss, since these beads are likely to constitute a polydisperse mixture of beads of varied sizes. In the recovery, the smallest fraction may perhaps pass through the filter and be lost. A gel which for instance can be cut into thin slices combines two advantageous properties: a large active surface (as opposed to cast cubes) with simultaneous ease of recovery (as opposed to polydisperse beads). Moreover, the cutting provides a section surface with open pores, thus ensuring contact between the enzyme and the reaction solution. In contrast, the casting method yields gels with closed pores. Also the preparation of droplets (beads) is likely to produce a surface having closed pores, because the hydrophobic parts of the gelatiniser will be directed outwards towards the surface of the droplet.

Although the invention has been described here with reference to a particular type of reaction and a specific gelatiniser, the invention is by no means limited to these conditions. On the contrary, the invention shall be considered to comprise all the applications and embodiments disclosed in the accompanying claims.

What is claimed is:

1. A gel containing an immobilized enzyme, comprising a water-soluble enzyme, a water-soluble gelatin and water, wherein a ratio of the amount of gelatin to the amount of water is selected such that the gel is capable of being mechanically divisible into dimensionally substantially stable fragments at a temperature which may reach a lower limit of the gelation temperature range of the gelatin, wherein said gel has a 30 to 50% gelatin concentration.

2. The gel of claim 1, wherein said gel has a 30 to 44% gelatin concentration.

3. The gel of claim 1, wherein said enzyme is lipase.

4. The gel of claim 1, wherein said lower limit of the gelation temperature range of the gelatin is 30° C.

5. A process for preparing the gel of claim 1, comprising i) adding water to a water-soluble enzyme and a water-soluble gelatin to form a mixture;

ii) heating said mixture to a temperature at which the gelatin dissolves, thereby forming a solution; and iii) cooling said solution until it forms a gel capable of being mechanically divided into dimensionally substantially stable fragments at a temperature that may reach a lower limit of the gelation temperature range of the gelatin, wherein said gel has a 30 to 50% gelatin concentration.

6. The process of claim 5, wherein said lower limit of the gelation temperature range of the gelatin is 30° C.

7. A process for performing an enzyme-catalyzed reaction, comprising adding a fragment of the gel of claim 1 to a reaction mixture consisting of reactants dissolved in a hydrophobic solvent; so as to catalyze a reaction and thereby produce a desired reaction product.

8. The process of claim 7, wherein said enzyme comprises lipase.

9. The process of claim 8, wherein said enzyme-catalyzed reaction comprises a synthesis of optically active isomers of an ester from an alcohol and an acid, with either the alcohol or the acid being a racemic mixture or an enantiomer.

10. The process of claim 8, wherein said enzyme-catalyzed reaction is a hydrolysis of an ester which is either a racemate or a pure enantiomer.

11. The process of claim 8, wherein said enzyme-catalyzed reaction is a transesterfication.

* * * * *